United States Patent [19]

Tallentire et al.

[11] Patent Number: 5,004,645
[45] Date of Patent: Apr. 2, 1991

[54] BARRIER PRODUCTS

[75] Inventors: Alan Tallentire, Cheshire; Colin S. Sinclair, Manchester, both of Great Britain

[73] Assignee: DRG (UK) Limited, Bristol, Great Britain

[21] Appl. No.: 381,675

[22] PCT Filed: Nov. 20, 1987

[86] PCT No.: PCT/GB87/00833
§ 371 Date: Jul. 13, 1989
§ 102(e) Date: Jul. 13, 1989

[87] PCT Pub. No.: WO88/03972
PCT Pub. Date: Jun. 2, 1988

[30] Foreign Application Priority Data
Nov. 22, 1986 [GB] United Kingdom ............... 8628808

[51] Int. Cl.⁵ ........................................... B32B 9/00
[52] U.S. Cl. ................................ 428/323; 428/537.5; 428/908; 427/244; 206/363; 206/438; 206/439
[58] Field of Search ............. 428/285, 323, 537.5, 428/908; 427/244; 206/363, 438, 439

[56] References Cited

U.S. PATENT DOCUMENTS 3,238,056  3/1966  Pall et al. .................... 427/244
3,591,010  7/1971  Pall et al. .................... 210/493
4,046,939  9/1977  Hart ............................. 428/311
4,084,949  4/1978  Biggins ........................ 55/524
4,099,943  7/1978  Fischman et al. ............ 55/417
4,522,843  6/1985  Kundrat ....................... 427/27

FOREIGN PATENT DOCUMENTS

3515025  10/1986  Fed. Rep. of Germany .
  03972   6/1988  PCT Int'l Appl. .
 860992   2/1961  United Kingdom .
1004447   9/1965  United Kingdom .
2099872  12/1982  United Kingdom .

Primary Examiner—Patrick J. Ryan
Attorney, Agent, or Firm—Larson and Taylor

[57] ABSTRACT

A porous material, e.g. a paper, has pores with a range of sizes. A pore modifying agent comprising particles of a narrow size range is selectively incorporated within the larger pores to provide zones of high surface area. These greatly reduce the penetrability of the material, e.g. by mirco-organisms, while having relatively little effect on its air-permeability. The modifying agent may be incorporated by creating a pressure difference across the material, and treating it with a dispersion, e.g. an aerosol, of the modifying agent, under conditions of low inertia, and incorporating only a small amount of the agent, e.g. not more than 1% w/w.

15 Claims, 8 Drawing Sheets

BARRIER PRODUCTS

The present invention relates to barrier products (generally comprising barrier webs) and to a method of producing such barrier materials.

There are many uses for materials which act as a barrier to the passage of air-borne micro-organisms or particulate dispersions whilst still retaining air-permeability.

For example, medical and surgical items are generally supplied in a sterile state enclosed within individual packages fabricated in part from porous material (e.g. paper, polymeric web or other non-woven material). Such porous materials are of necessity permeable to gases and vapours so as to permit sterilisation of the item (after packaging) by means of steam or a gas such as ethylene oxide. Furthermore permeability to air is important to allow the application of a vacuum during sterilisation to facilitate the packaging process and to limit the air volume around the packaged item. However, in spite of this air-permeability, the material must act as an effective barrier to the passage of micro-organisms so that the packaged item remains sterile.

Other examples of air-permeable barrier materials which are used in the medical field include drapes, wrapping materials, clean room clothing, and face masks. Further examples of barrier products are filter media (e.g. HEPA filters) used to provide clean environments in, for example, the pharmaceutical, medical, electronic and energy industries.

Effective barrier materials as described above may be difficult and expensive to produce. Furthermore microbiological barrier materials presently available vary considerably in their ability to stop microorganisms. For example, one commercially available paper used as a packaging material for sterile medical and surgical items shows a level of penetration of around 20% when challenged with a dispersion of bacterial spores flowing at a rate of $6 \times 10^{-3}$ dm$^3$ min$^{-1}$ cm$^{-2}$ whereas another commercially available paper shows a level of penetration of around 0.001% when challenged under similar conditions.

It is therefore an object of the present invention to provide barrier materials which are highly effective against the passage of micro-organisms or air-borne particulate dispersions and which may be produced comparatively easily and cheaply.

According to a first aspect of the present invention there is provided an air-permeable barrier material comprising porous material having pores with a range of sizes wherein a pore modifying agent is selectively incorporated in the pores at the upper end of the size range, said pores constituting a minor proportion of the total number; said modifying agent being such as to provide zones of high surface area within these pores in such a way as to restrict the passage of air-borne particles through these pores. It can be arranged that the incorporation of the modifying agent has little or no effect on the permeability of the porous material, because the incorporation is effected without substantially reducing the pore sizes and/or because the air-permeability of the material is substantially provided by the smaller pores which incorporate substantially none of the modifying agent.

Preferably the modifying agent is of at least one substantially uniform particle size (as explained below).

The term 'pore' is used herein to include any passageway or interstice that extends from one major face to an opposed major face of the material.

Typical air-borne particles against which the barrier material of the invention is effective are microorganisms.

According to a second aspect of the present invention there is provided a method of enhancing the barrier performance of an air-permeable material having a range of pore sizes, the method comprising establishing a pressure differential across the material and treating the higher pressure side of the material with a suspension, dispersion or aerosol of a pore modifying agent under conditions such that the pore modifying agent is selectively incorporated in the pores at the upper end of the size range (said pores constituting a minor proportion of the total number) so as to provide zones of high surface area within these pores in such a way as to restrict the passage of air-borne particles through these pores. The pore modifying agent is preferably of at least one substantially uniform particle size range.

The term 'pore size' as used herein has its conventional meaning, i.e. for a given pore it is the minimum cross-sectional size throughout the length of the pore. Pore size may be determined by any conventional method.

The barrier material of the invention is a material having a structure with a range of pore sizes, e.g. as obtained during the production of paper from a dispersion of cellulose fibres, e.g. by a wet laying technique. In many such materials, the pores defined therein have differing sizes described by a log-normal distribution in which a small fraction of the total number of pores exhibits a markedly greater size as compared to the remainder. These large pores (often referred to as 'transport pores') are critical in determining barrier performance since it is these pores which principally allow the passage of air-borne micro-organisms or particles. In the barrier material of the invention the large pores are modified by the incorporation of the pore modifying agent therein in such a way as to provide zones of high surface area within the large pores which enhances significantly their ability to stop the passage of air-borne micro-organisms and particles. Nevertheless there may be little or no pore modifying agent present in the pores of smaller size. The product remains air-permeable. The selective incorporation of the pore modifying agent in the large pores may leave the material macroscopically unaffected.

In the barrier material of the invention, the pore modifying agent will generally be of a size significantly less than the maximum pore size of the untreated material and this maximum pore size may remain substantially unaltered (as compared to the untreated material) after treatment with the pore modifying agent, or, if reduced, may still be greater than the size of micro-organism or particle which the barrier material is intended to remove. The effectiveness of the barrier material therefore does not depend on a simple "sieving" of the micro-organism (or particle) resulting from clogging of the pores or reduction in size thereof, but is derived from the increase in surface area which the pore modifying agent provides within the pore.

Pore modifying agents used in the present invention desirably satisfy a number of criteria. In particular, they must be capable of being targetted into the pores at the upper end of the size range. This requirement may be met by using a pore modifying agent of substantially uniform size. (By substantially uniform size is meant that generally 90% of the mass of the pore modifying agent falls within a three fold particle size range.) This uniformity of size (which may be selected dependent on the material being treated) ensures that there is no significant amount of large particles of modifying agent which can clog the large pores. It is generally preferred that the pore modifying agent has a mean size less than one third (more preferably less than one fifth) the maximum pore size of the material being treated. It is however possible to use pore modifying agent of two or more different, substantially uniform size ranges should this be required for particular applications.

The amount of pore modifying agent incorporated in the material is generally insignificant as compared to original weight thereof (e.g. $\leq 1\%$ w/w; possibly up to 10% e.g. for light materials) but nevertheless the modification of the larger pores by the small amount of agent provides a significant improvement in barrier performance.

Preferably the pore modifying agent is a particle (liquid or solid) with a size of less than 50 microns, more preferably less than 6 microns. The actual particle size used will be dependent on the type of barrier material to be produced. Thus, for a filter medium a size range of 1-2 microns may be preferred whereas a different size range might be used for, say, barrier materials to be used for packaging of sterile items.

The pore modifying agent may be selected from a wide range of inanimate materials, for example inorganic materials such as clay, chalk or glass, organic material such as alkylketene dimer, and biological materials such as cellulose. Mixtures of two or more such materials may be used.

A preferred method of producing the barrier material of the invention is to treat one side of the porous material (of which the barrier properties are to be enhanced) with the pore modifying agent (or a precursor from which the pore modifying agent is derived) whilst causing the pore modifying agent (or precursor) to enter the material and be selectively incorporated in those pores of the material which are at the upper end of the pore size range. Preferably the pore modifying agent is in the form of a suspension or dispersion (preferably in air) in which the pore modifying agent is the discontinuous phase. Most preferably, the particulate pore modifying agent is used in the form of an aerosol having a droplet size of 0.5 to $10\mu$. The pore modifying agent is caused to pass into the material by establishing a pressure differential across the material in the form of either increased pressure at the side of the material to which the pore modifying agent is applied or reduced pressure at the side of the material opposite to that at which the pore modifying agent is applied. This method is based on the fact that the flow of the suspension, dispersion or aerosol through the pores of the material being treated is proportional to $r^4$ (where r is pore radius). Consequently there is a significantly greater flow through the pores of large cross-section than through those of small cross-section and the difference in flow ensures that substantially all of the pore modifying agent is targetted to the larger pores and becomes incorporated therein. It is envisaged that this method may be effected on a continuously moving web of material across which a pressure differential is applied.

The inertial conditions of the pore modifying process are an important factor in the treatment process. As described more fully below, the use of high inertia results in the pore modifying agent simply remaining on the surface of the material being treated since it is not able to follow the flow pattern into the pores. With conditions of lower inertia, the benefits of the invention will be obtained, although the actual properties obtained for the barrier material will depend on the inertia conditions affecting the pore modifying agent, again as detailed below.

The time for which the material is treated for enhancement of its barrier performance depends on factors such as the pressure differential across the material, the concentration of the pore modifying agent in the suspension, dispersion or aerosol and the degree of enhancement required. Generally however a substantial improvement in barrier performance is obtained with comparatively short treatment times and using only small amounts of pore modifying agent.

Most preferably the pore modifying agent is used as an aerosol. Such an aerosol may be generated by air dispersal of a solid pore modifying agent or by aerosolisation of a liquid suspension of the pore modifying agent. Alternatively it is possible to use an aerosol generated from a liquid or a solution from which the pore modifying agent is derived. A surface active agent may be used to assist formation of the aerosol.

Advantageously an adhesive agent is used in conjunction with the pore modifying agent to enhance retention thereof in the pores. The adhesive (e.g. latex) may be incorporated in the suspension, dispersion or aerosol with which the material is treated. Alternatively the material being treated may already possess an adhesive whose action may be initiated by a physical or chemical process after the material has been treated with pore modifying agent. The adhesive may be one which is activated by heat.

A wide variety of air-permeable materials may be treated by the method of the invention for various end uses. They may have been produced by wet laying techniques, but this is not essential. Preferably, the air-permeable material is a woven or non-woven material, e.g. a paper, textile, mat board or film (e.g. a spun-bonded film). The material may comprise fibers which may be selected from cellulose fibers, synthetic fibers, glass fibers, mineral fibers and ceramic fibers. Mixtures of fibers may also be used.

As a specific example, porous web materials (e.g. cellulose papers polymeric webs and other non-woven materials) of a variety of specific weights may be treated for their subsequent use as packaging material for medical or surgical items. Non-woven material may be treated for use as drapes, wrapping materials, clean room clothing and face masks for medical uses. Furthermore, HEPA filters, depth filters and other filter media may be produced by treatment of appropriate materials.

It will thus be appreciated that the method of the invention may be used to produce effective barrier materials from either readily available substrates or custom designed materials defined by reference to porous composition and properties with respect to perceived pore sizes.

The invention will be further described by way of example only with reference to the accompanying drawings, in which:

BRIEF DESCRIPTION OF THE DRAWINGS

FIG. 1 illustrates the form of a typical distribution of pore sizes in a wet-laid material;

FIG. 2 diagrammetically illustrates one embodiment of apparatus for carrying out the method of the invention.

Figure 1:
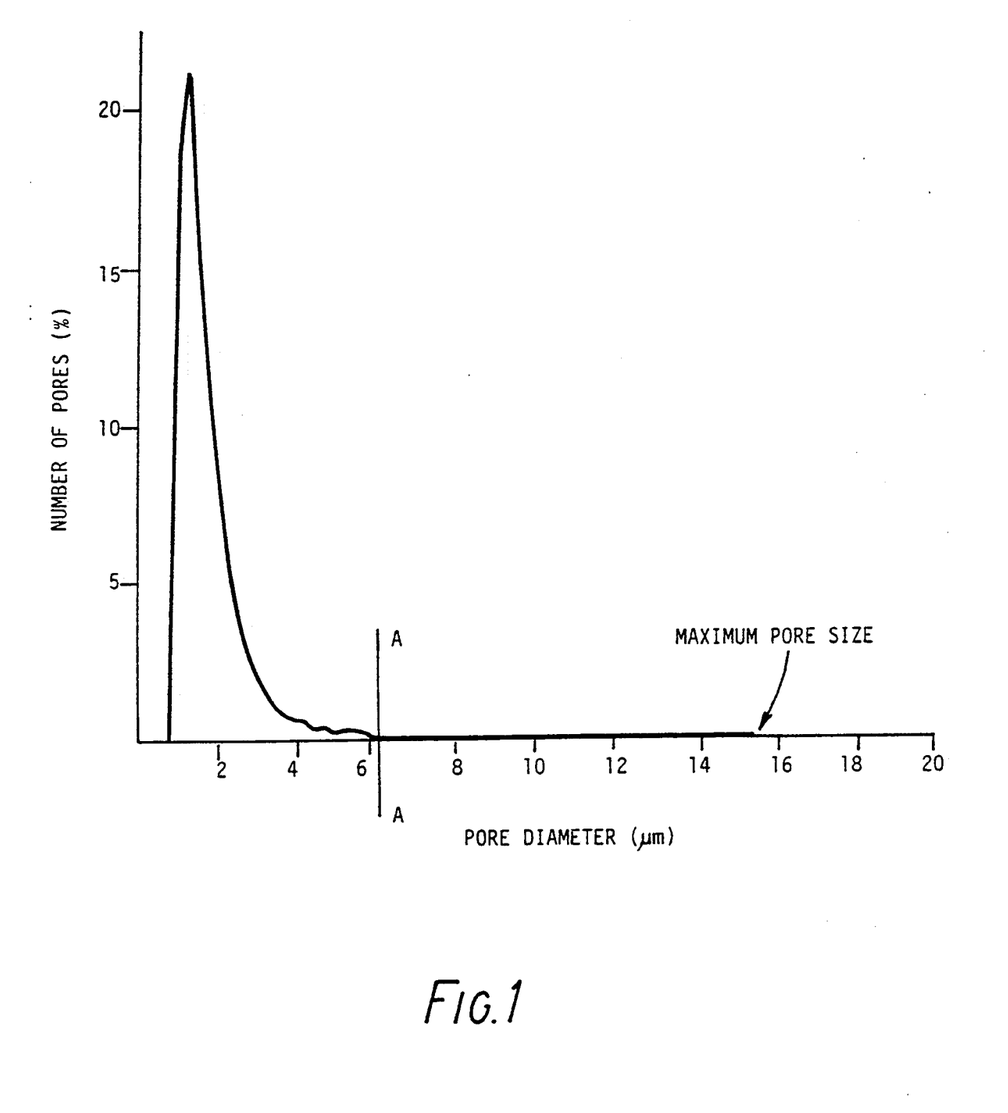

FIG. 1 illustrates the form of typical log-normal distribution of pore sizes in a wet-laid material comprised of randomly orientated fibres. A method embodying the invention may cause modification of all pores having a pore size to the right of the illustrated cut-off line A—A shown in the Figure. The exact position of line A—A will depend on factors such as treatment time, flow rates through the material, and the size and concentration of pore modifying agent in the aerosol. For example with increasing treatment time for a given set of treatment conditions the line A—A will be moved further to the left in the illustrated graph.

Figure 2:
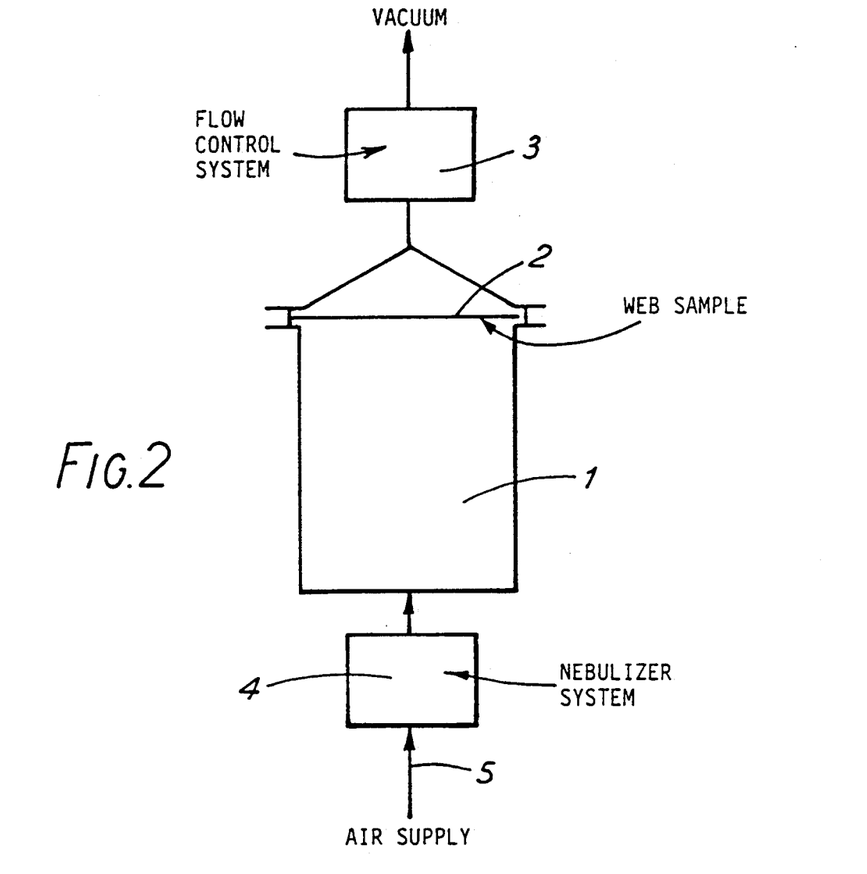

The apparatus illustrated in FIG. 2 comprises a treatment chamber 1 in which a sample 2 of material to be treated is supported as shown. A flow control system 3 serves to establish a pressure differential across the material 2 whereas a Hudson nebuliser 4 associated with an air supply line 5 is provided at the other side. In use of the appartus, an aerosol of the pore modifying agent is generated in the nebuliser 4 and is drawn through the material 2 by virtue of the applied vacuum. As explained above, the pore modifying agent is selectively located in the larger pores of the material thus enhancing the barrier properties of the material.

Figure 3:
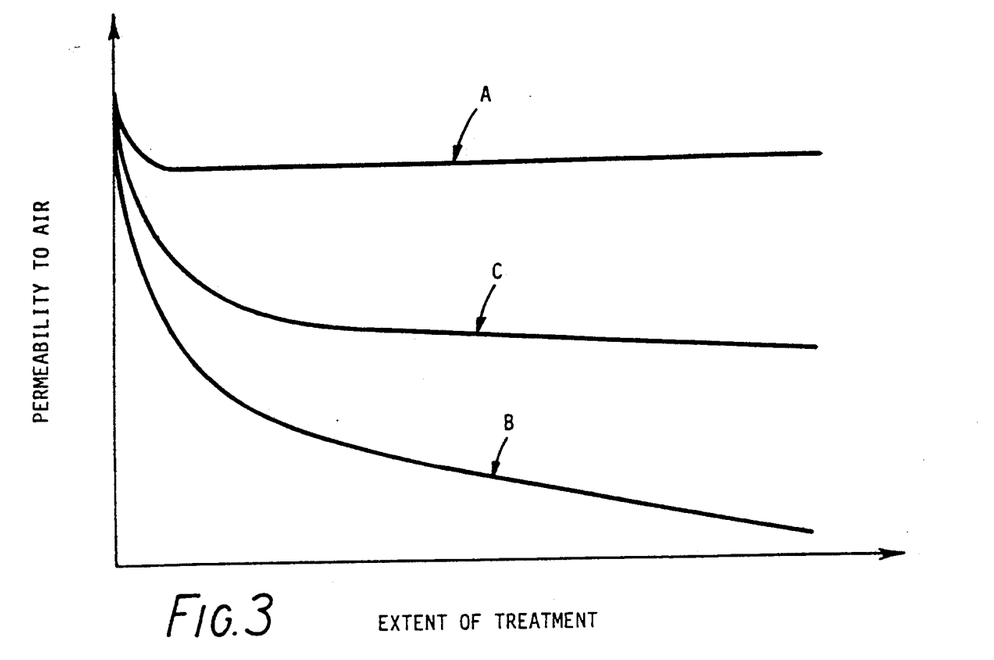
FIG. 3 is an idealised graph of air-permeance vs extent of treatment for the low, medium and high inertia treatment.
Figure 4:
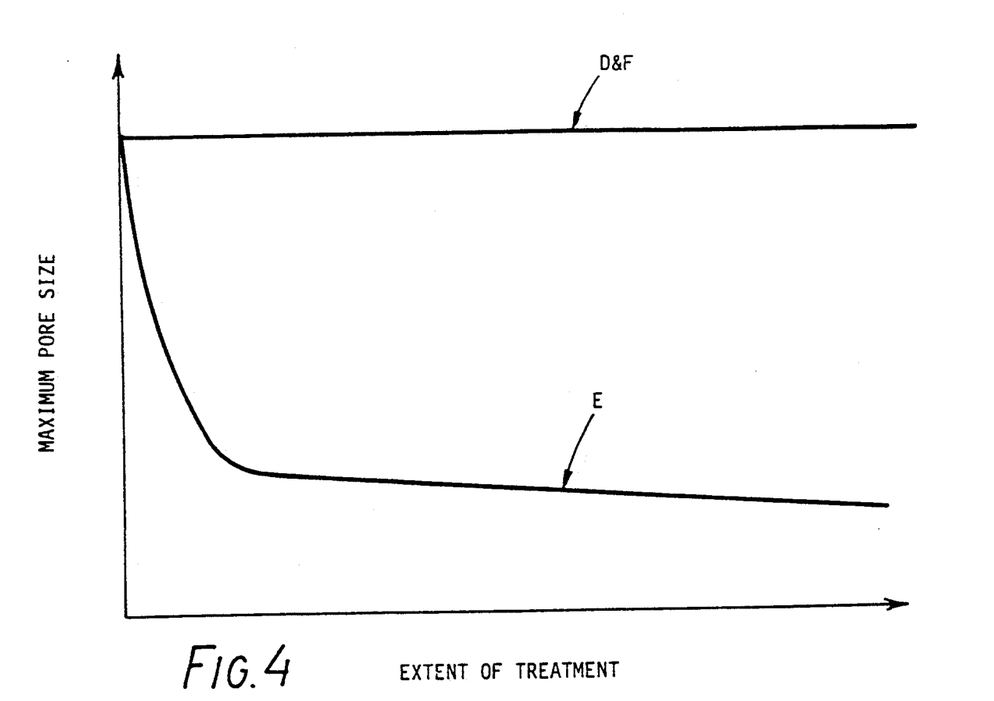
FIG. 4 is an idealised graph of maximum pore size vs extent of treatment for the low, medium and high inertia treatments.

The inertial conditions of the pore modifying treatment have been found to affect significantly the properties obtained for the treated material. FIG. 3 is an idealised graph (based on actual results) for air-permeance of a given material vs extent of treatment at high inertia (curve A), medium inertia (curve B) and low inertia (curve C). FIG. 4 is an idealised graph (again based on actual results) of maximum pore size vs extent of treatment at high inertia (curve D), medium inertia (curve E), and low inertia (curve F - shown as coincident with curve D).

The inertia of the pore modifying agent is directly dependent upon the mass and flow rate of the particles and inversely related to the size of pores of the material being treated.

Embodiments of the invention use a low degree of treatment, so that only a small amount of modifying agent is incorporated. For low inertia treatment, there is substantially no reduction of maximum pore size (with increasing extent of treatment (curve F)) but there is a reduction of air-permeance (curve C). At medium inertia, there is a reduction of maximum pore size (curve E) and a reduction of air-permeance (curve B) greater than that obtained at low inertia treatment. At high inertia, there is substantially no reduction of air-permeance (curve A) and substantially no reduction of pore size (curve D). This is because of the small amount of modifying agent used. With large amounts (particularly at high inertia), the pore modifying agent would be impregnated onto and into the top surface to form a dusting or coating, so that pore size and air-permeance would fall. This is because the pore size would then be determined by the size of pore openings, governed by the nature of the dusting. That is, pores are then clogged at the surface.

Figure 5A:
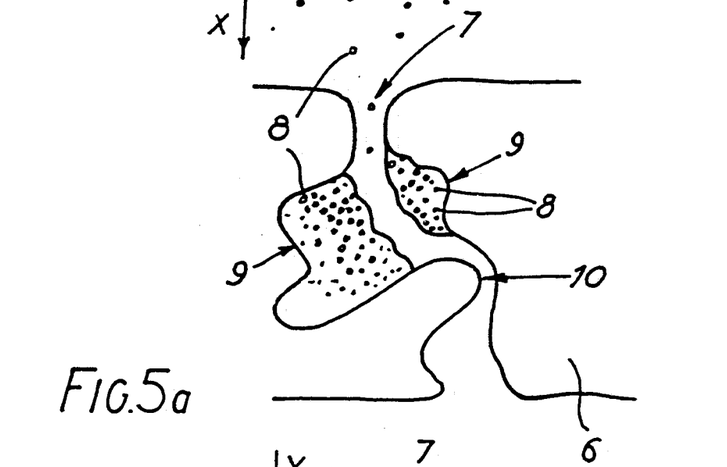
FIGS. 5a, 5b and 5c each illustrate a pore of a material which has been treated with a pore modifying agent at low, medium and high inertia respectively, the latter procedure being outside the scope of the invention.
Figure 5B:
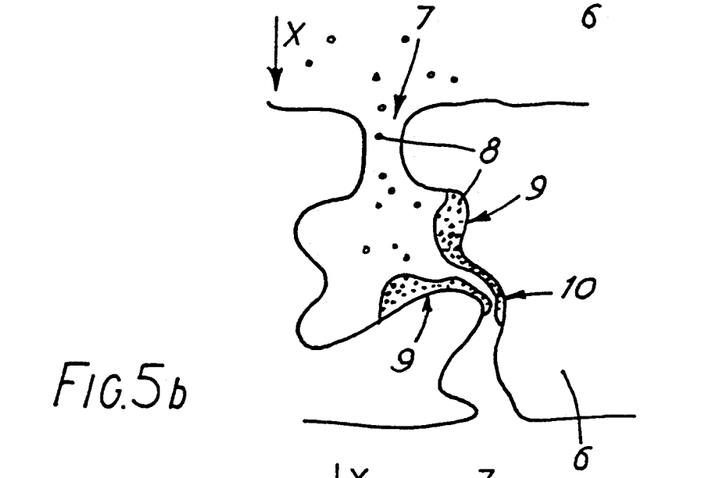
Figure 5C:
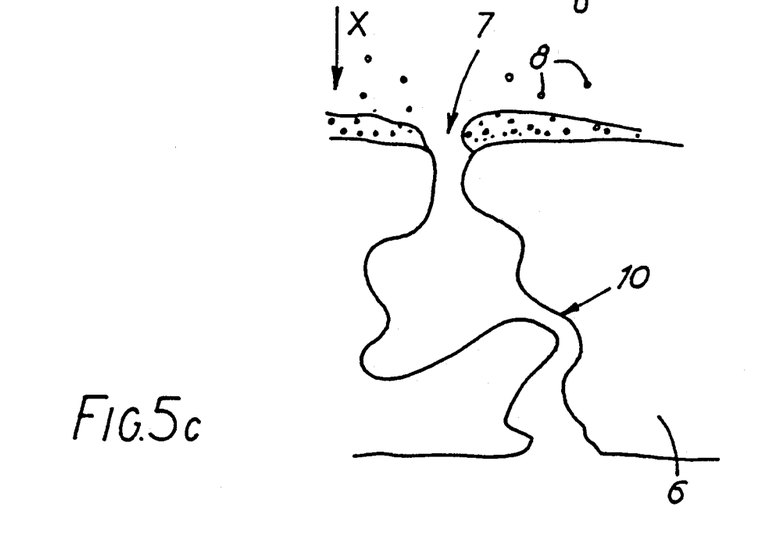

FIGS. 5a, 5b and 5c show the way in which we believe the pore modifying agent is deposited in or on the material being treated using low, medium and high inertias for the pore modifying agent respectively. In each of these Figures, the material is referenced at 6, a transport pore therein as 7, and the particulate pore modifying agent as 8. Typically, the pore 7 will comprise one or more chambers 9 and one or more "constrictions" 10, the smallest of which is the minimum cross-section of the pore which determines the pore size.

In the low inertia case of FIG. 5a, the pore modifying agent 7 (which moves towards the material 6 in the direction of arrow X) follows the flow stream and enters chamber 9 of pore 7 where it is held as shown by Brownian Motion capture. Consequently substantially all of the pore modifying agent is located in chamber 9 where it provides an increase in surface area. Since substantially none of the pore modifying agent locates at the constriction 10 there will be no reduction in the measured pore size of the material. There will however be a slight reduction in the air-permeance of the treated material due to the presence of the pore modifying agent in chamber 9.

In the case of treatment at medium inertia (as depicted in FIG. 5b), the momentum of the pore modifying agent is too great for Brownian Motion capture in chamber 9. The particles do however leave the flow stream by impaction on the walls of the pore in the region of, and at, the constriction 10. Deposition at constriction 10 reduces the measured pore size and there is a reduction of air-permeance greater than that for low inertia treatment because pore modifying agent reduces the minimum cross-sectional size of the pore.

For high inertia treatment, the pore modifying agent is unable to follow the flow stream into the pore 7 and impacts on the surface of the material to form a dusting thereon. For treatments with amounts of modifying agent too small to cause dusting over a substantial amount of the surface (with clogging of pore mouths sufficient to reduce the pore size), there is thus no reduction in pore size and no reduction in air-permeance. However, high levels of treatment at high inertia will lead to a layer of modifying agent on and in the top surface of the material, resulting in reduction in pore size openings and thus in reduced air-permeance.

It is only the materials which have their pores modified as shown in FIGS. 5a and 5b which have an improved barrier performance due to presence of zones of high surface area within pores. Thus, high inertia treatments resulting in surface clogging are to be avoided.

The improvement in barrier performance arises principally from the increased surface area within the pore (as provided by the pore modifying agent) which has a severalfold effect. Firstly, any micro-organism or other particle which enters the pore may follow an air-flow path through the pore. However, forces of diffusion and impaction will cause the micro-organisms to leave the flow and be captured by the deposited pore modifying agent thereby preventing its passage through the barrier material. Secondly, the presence of the pore modifying agent may provide a hindrance to air flow through the pore which is thereby reduced. Consequently, there is less probability of particles entering the pore.

The following Examples are provided to illustrate the invention. All Examples were carried out using the apparatus illustrated in FIG. 2 working under the following conditions:

Input pressure to nebuliser: 20 psi
Concentration of pore modifying agent in aerosol: 3 mg/dm$^3$
Sample size of material: 78.5 cm$^2$.

EXAMPLE 1

A 60 g/m$^2$ paper of low air-permeance (about 100 Bendtsen) was treated with an aerosol generated in nebuliser 4 from a suspension of clay in water, the suspension having the following composition:
clay: 50% w/v
latex adhesive: 10% w/v
calgon (dispersant): 0.5% w/v
water: to 100%.

Figure 6:
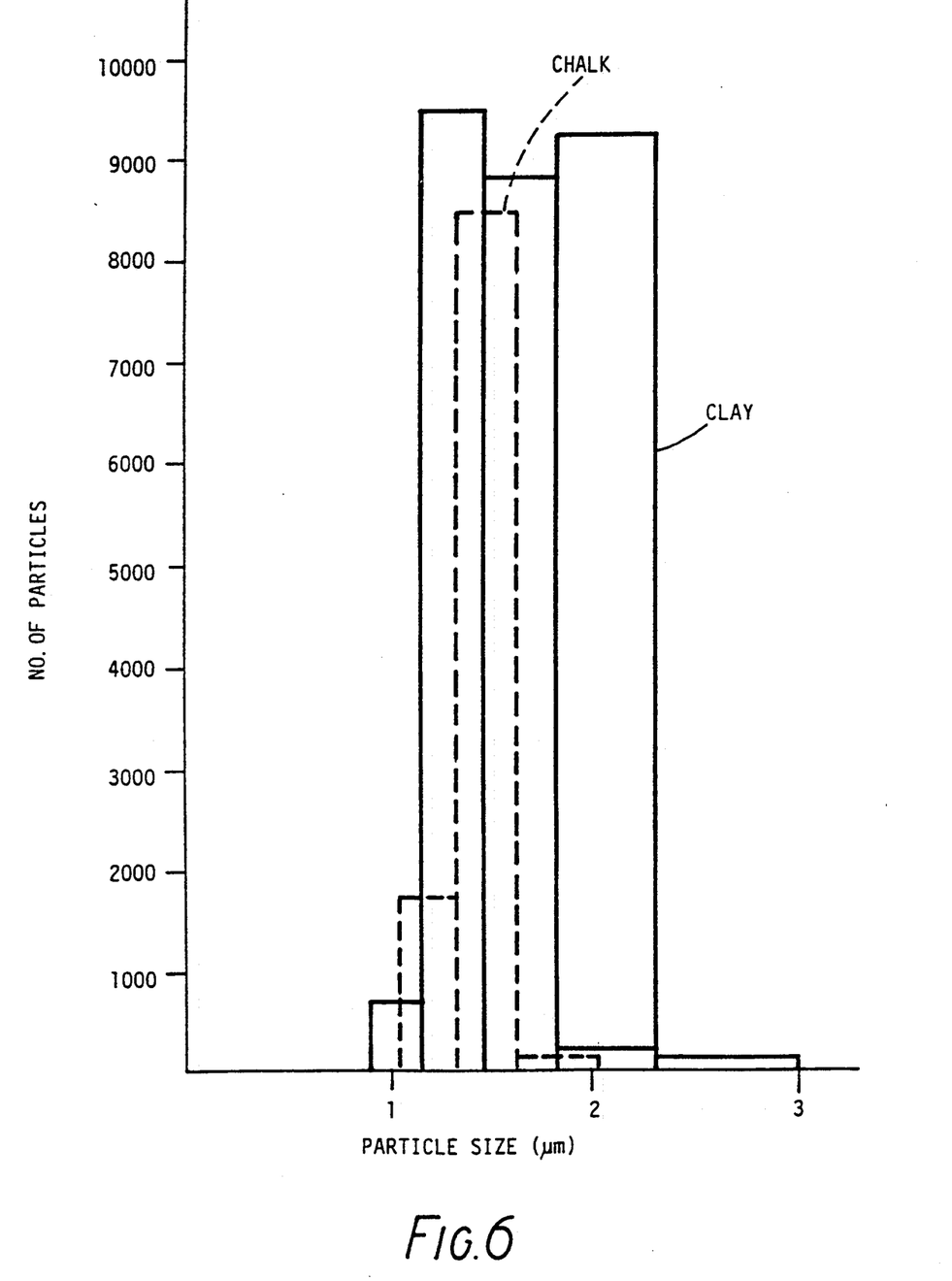
FIG. 6 shows particle size distributions for clay and chalk used as pore modifying agents in the Examples.

The clay had the substantially uniform particle size distribution shown in FIG. 6.

Figure 7:
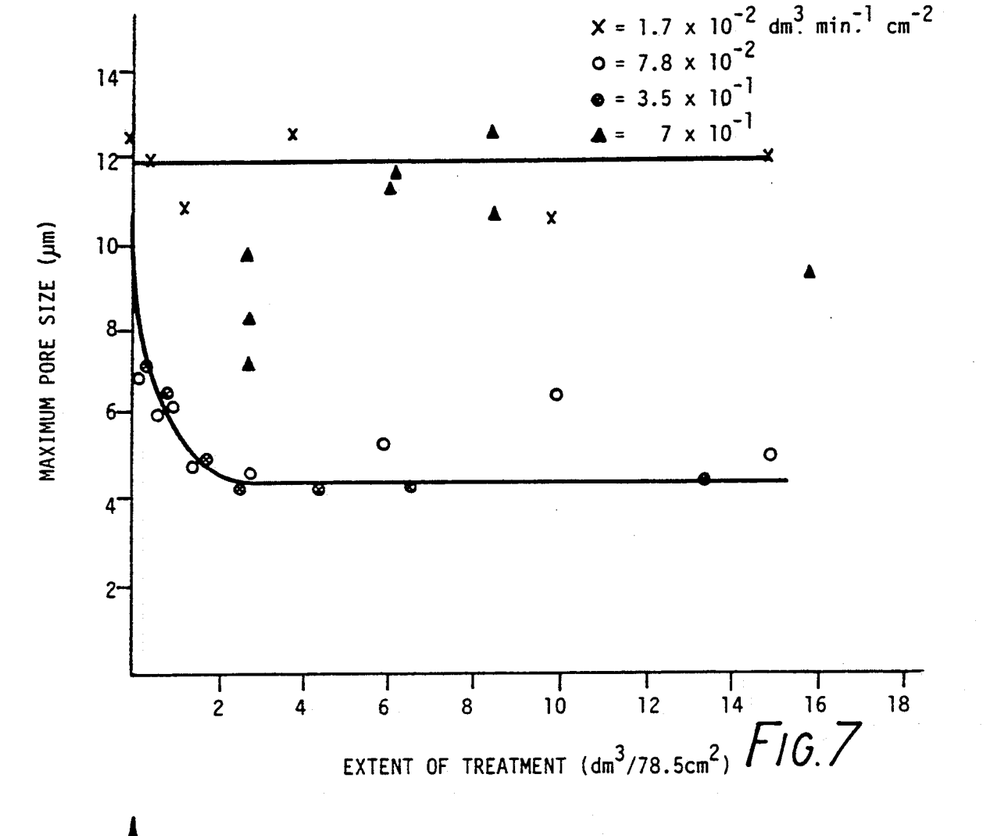
FIGS. 7 to 12 are graphs showing the results of the Examples detailed below.
Figure 8:
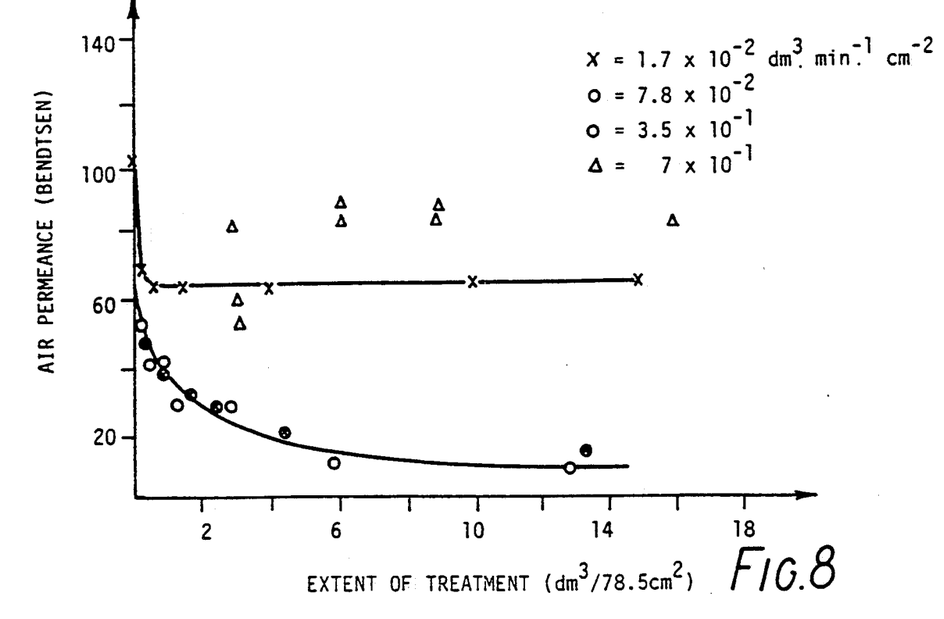

The method was carried out for varying treatment times at each of several different rates of flow across the material using different samples of the material (cut from the same web) so as to give different extents of treatment. The results are shown in FIGS. 7 and 8 which are respectively graphs of maximum pore size vs extent of treatment and air-permeance (Bendtsen) vs extent of treatment. FIG. 7 shows the reduction in maximum pore size for the intermediate rates of flow used ($7.8 \times 10^{-2}$ and $3.5 \times 10^{-1}$ dm$^3$ min$^{-1}$ cm$^{-2}$) but the maintenance of maximum pore size at the low ($1.7 \times 10^{-2}$ dm$^3$ min$^{-1}$ cm$^{-2}$) and high ($7 \times 10^{-1}$ dm$^3$ min$^{-1}$ cm$^{-2}$) flow rates. The scattering of results for the high inertia case results from random variation of pore size since there was insufficient modifying agent for uniform surface coating. FIG. 8 shows the reduction in air-permeance at the low and intermediate flow rates, and the substantially constant air-permeance at the high flow rate (of FIGS. 3 and 4).

EXAMPLE 2

Figure 9:
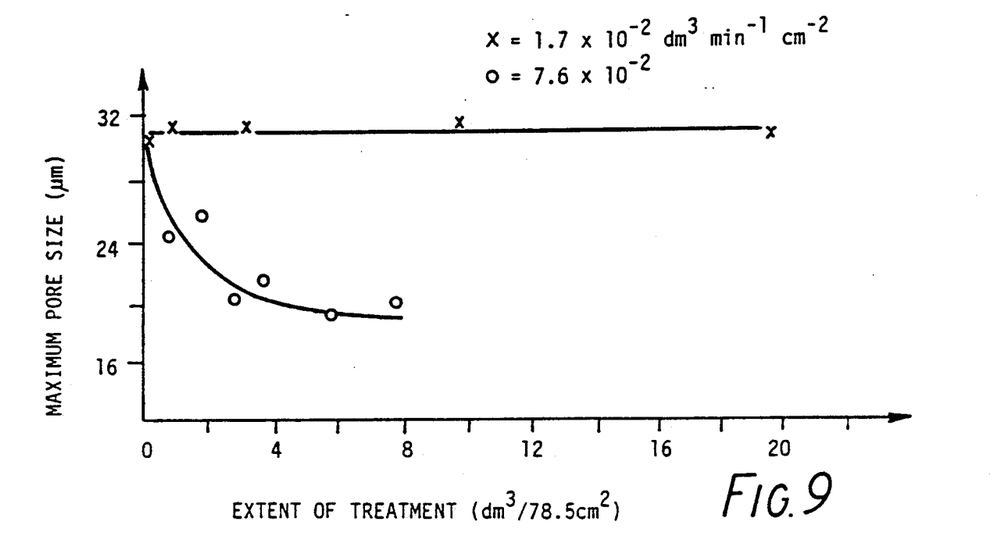
Figure 10:
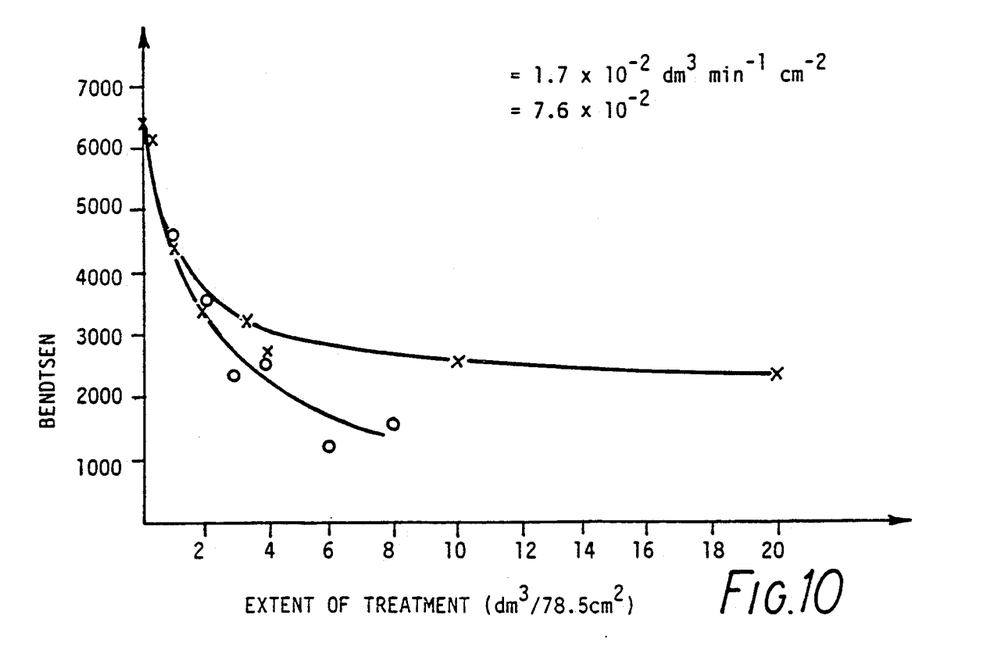

This was generally a repeat of Example 1 but using a different 60 g/m$^2$ paper, of high air-permeance (about 6500 Bendtsen). The results (and the flow rates used) are shown in FIGS. 9 and 10. Once again, the variation of air-permeance and maximum pore size is clear from these graphs.

EXAMPLE 3

Samples of a third 60 g/m$^2$ paper of medium air-permeance (about 350 Bendtsen) were each treated with an aerosol comprising clay as pore modifying agent at a flow rate across the material of $1.7 \times 10^{-2}$ dm$^3$ min$^{-1}$ cm$^{-2}$ for varying treatment times thereby giving different extents of treatment (and thus different air-permeances). Fresh samples of the material were also treated (for various times) at a flow rate of $7.8 \times 10^{-2}$ dm$^3$ min$^{-1}$ cm$^{-2}$.

Figure 11:
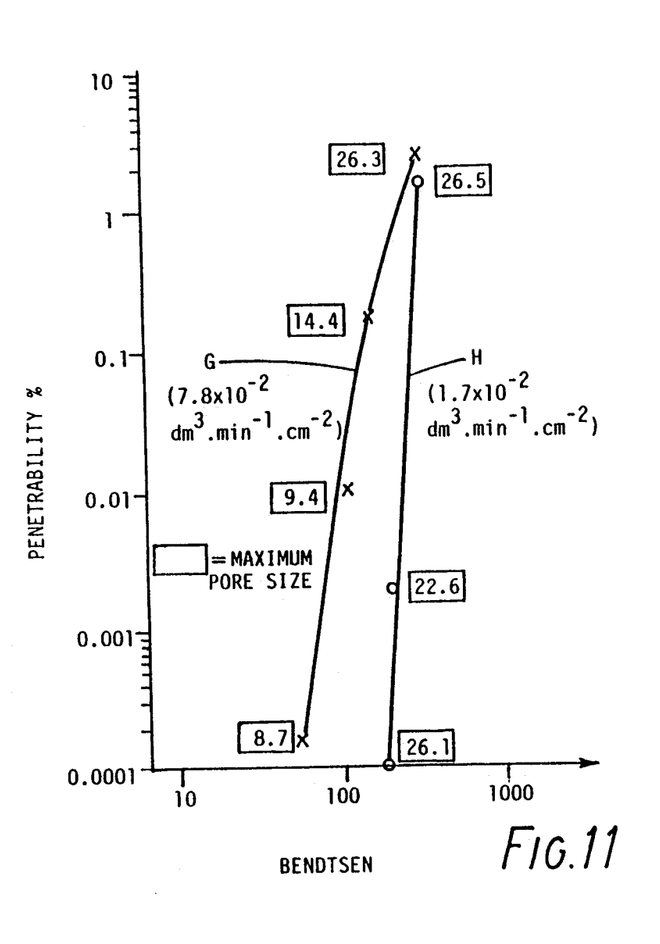

The treated samples thus obtained were then individually challenged under the same conditions with air-borne micro-organisms at a challenge flow rate of $6.5 \times 10^{-3}$ dm$^3$ min$^{-1}$ cm$^{-2}$ and the percentage penetration of such micro-organisms through the web determined. The results are shown in FIG. 11 which is a graph of percentage penetration vs air-permeance (Bendtsen) (both plotted on a logarithmic scale). In FIG. 11, the points represented by a "X" are those samples treated with the pore modifying agent at a flow rate of $7.8 \times 10^{-2}$ dm$^3$ min$^{-1}$ cm$^{-2}$ (curve G) and those represented by a "O" the samples treated at $1.7 \times 10^{-2}$ dm$^3$ min$^{-1}$ cm$^{-2}$ (curve H).

The explanation for these two curves resides in the location of the zone of high surface area formed by deposition of pore modifying agent within transport pores. Under conditions of low inertia (curve H), percentage penetration is seen to fall dramatically with slight reduction in air-permeance. This is in keeping with enhancement of barrier properties by formation of a zone of high surface area within pore chambers without reducing pore size. On the other hand, under conditions of medium inertia (curve G), percentage penetration is seen to fall dramatically with greater reduction in air-permeance compared with low inertia conditions. This is in accord with enhancement of barrier properties by formation of a zone of high surface area at pore constrictions. Under these conditions, in addition to increased barrier properties, the zone of high surface area leads to a reduction in pore size which, in turn, gives decreased air-permeance. The change in pore size under condition of medium inertia is evident from a decrease in maximum pore size (see values of maximum pore size in boxes on FIG. 11).

EXAMPLE 4

A fourth paper of 60 g/m$^2$ grammage and low air-permeance (about 100 Bendtsen) was treated with an aerosol generated in nebuliser 4 from a suspension of chalk in water, the suspension having the following composition.
chalk: 50% w/v
latex adhesive: 10% w/v
calgon (dispersant): 0.5% w/v
water: to 100%.

The chalk had the substantially uniform particle size distribution shown in FIG. 6.

The method was repeated for varying treatment times using different samples (cut from the same paper web) so as to give different extents of treatment (expressed as dm$^3$). The various treated samples (as well as an untreated sample) were then individually challenged under the same conditions with air-borne micro-organisms and the percentage penetration of such micro-organisms through the web determined. The results are graphically depicted in FIG. 12 in which percentage penetration of micro-organisms (on a logarithmic scale) is plotted against extent of treatment.

Figure 12:
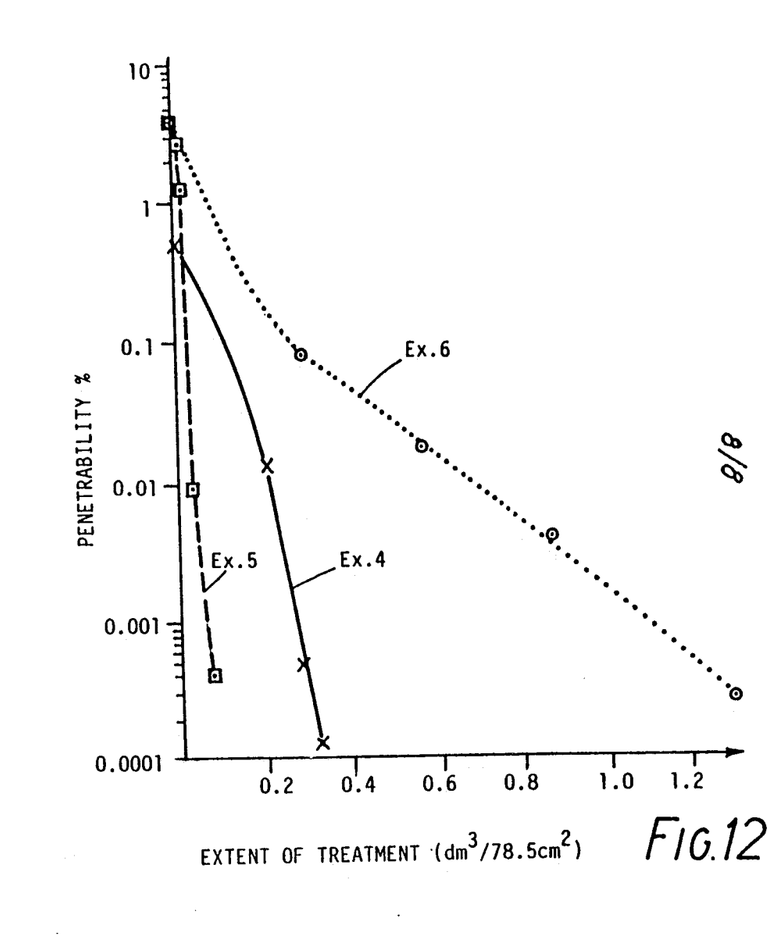

It will be immediately apparent from FIG. 12 that the percentage penetration of 0.4% for the untreated sample drops markedly to a value of about 0.0002% for an extent of treatment less than 1 dm$^3$ (indeed, less than 0.4).

EXAMPLES 5 AND 6

These were generally similar to Example 1, using similar aerosol compositions. Example 5 used 60 g/m$^2$ paper of medium air-permeance (about 450 Bendtsen). Example 6 used 45 g/m$^2$ paper of medium air-permeance (about 500 Bendtsen). Both papers had penetrability values of 4%. FIG. 12 shows how these were reduced by different extents of treatment. The penetrability of the heavier paper (Ex. 5) was reduced to 0.0004 by treatment of only about 0.1 dm$^3$/78.5 cm$^2$. The penetrability of the lighter paper (Ex. 6) was similarly reduced (to 0.0003%) but this required more treatment (1.3 dm$^3$/78.5 cm$^2$).

We claim:

1. An air-permeable barrier material comprising porous material having pores with a range of sizes wherein a pore modifying agent is selectively incorporated in a minor proportion of the total number of the pores, said minor proportion being at the upper end of said range of sizes; said modifying agent being such as to provide zones of high surface area within said pores at the upper end of said range in such a way as to restrict the passage of air-borne particles through said pores at the upper end of said range; and wherein the pore modifying agent comprises particles of substantially uniform size, at least 90% of said particles having diameters falling within a three-fold size range.

2. An air-permeable barrier material according to claim 1 wherein the pore modifying agent consists of particles whose mean size is less than ⅓ the maximum pore size.

3. An air-permeable barrier material according to claim 1 wherein the weight of pore modifying agent is not more than 1% of the weight of said porous material.

4. An air-permeable barrier material according to claim 1 wherein said porous material comprises paper.

5. An air-permeable barrier material according to claim 1 wherein the porous material is substantially composed of fibres.

6. An air-permeable barrier material according to claim 1 wherein the pore modifying agent is selected from chalk, clay, glass, cellulose and alkylketene dimers.

7. An air-permeable barrier material according to claim 1 wherein said pores include a minor proportion of transport pores which exhibit a markedly greater size as compared with the remaining pores and, in use in the absence of modifying agent principally allowing the passage of air-borne particles; and wherein said pore modifying agent is located in said transport pores.

8. An air-permeable barrier material according to claim 1 wherein the disposition of the pore modifying agent within the pores is such that the pore size of the pores in which said pore modifying agent is incorporated is substantially unaffected by its presence.

9. An air-permeable barrier material according to claim 1 wherein the pore modifying agent is located in said pores at constrictions thereof so as to form zones of high surface area at and adjacent the constrictions.

10. A package comprising a medical or surgical item enclosed in packaging comprising an air-permeable barrier material comprising porous material having pores with a range of sizes wherein a pore modifying agent is selectively incorporated in a minor proportion of the total number of the pores, said minor proportion being at the upper end of said range of sizes; said modifying agent being such as to provide zones of high surface area with said pores at the upper end of said range in such a way as to restrict the 11. A method of enhancing the barrier performance of an air-permeable material having pores with a range of sizes, the method comprising:

establishing a pressure differential across the material;

providing at the higher pressure side of the material a suspension, dispersion or aerosol of a pore modifying agent, wherein the pore modifying agent comprises particles of substantially uniform size, at least 90% of said particles having diameters falling within a three-fold size range; and maintaining said pressure differential under conditions such that the pore modifying agent is selectively incorporated in a minor proportion of the total number of the pores, said minor proportion of pores being pores at the upper end of said range, so as to provide zones of high surface area within said pores at the upper end of said range in such a way as to restrict the passage of airborne particles through said pores at the upper end of said range.

12. A method according to claim 11 wherein said pore modifying agent is provided at said higher pressure side of the porous material as an aerosol.

13. A method according to claim 11 wherein said pressure differential is maintained under conditions of low or medium inertia.

14. A method according to claim 11 wherein said suspension, dispersion or aerosol includes an adhesive to retain the pore modifying agent in the porous material.

15. A method according to claim 11 wherein said pressure differential is maintained under conditions of inertia such that the disposition of the pore modifying agent within the pores is such that the pore size of the pores in which said pore modifying agent is incorporated is substantially unaffected by its presence.

* * * * *

UNITED STATES PATENT AND TRADEMARK OFFICE
CERTIFICATE OF CORRECTION

PATENT NO. : 5,004,645
DATED : April 2, 1991
INVENTOR(S) : TALLENTIRE, ET AL.

It is certified that error appears in the above-identified patent and that said Letters Patent is hereby corrected as shown below:

Item [30] in the title page should read as follows:

[30]   Foreign Application Priority Data

November 22, 1986 [GB] United Kingdom      8628008

Signed and Sealed this

Second Day of March, 1993

*Attest:*

STEPHEN G. KUNIN

*Attesting Officer*           *Acting Commissioner of Patents and Trademarks*